US011992036B2

(12) United States Patent
Longo et al.

(10) Patent No.: US 11,992,036 B2
(45) Date of Patent: *May 28, 2024

(54) FASTING CONDITION AS DIETARY TREATMENT OF DIABETES

(71) Applicant: UNIVERSITY OF SOUTHERN CALIFORNIA, Los Angeles, CA (US)

(72) Inventors: Valter D. Longo, Playa del Rey, CA (US); Chia-Wei Cheng, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 169 days.

This patent is subject to a terminal disclaimer.

(21) Appl. No.: 17/162,809

(22) Filed: Jan. 29, 2021

(65) Prior Publication Data

US 2021/0145038 A1 May 20, 2021

Related U.S. Application Data

(63) Continuation of application No. 16/592,299, filed on Oct. 3, 2019, now Pat. No. 10,932,486, which is a continuation of application No. 15/204,156, filed on Jul. 7, 2016, now Pat. No. 10,433,576, which is a continuation of application No. 14/320,996, filed on Jul. 1, 2014, now Pat. No. 9,386,790.

(60) Provisional application No. 61/841,709, filed on Jul. 1, 2013.

(51) Int. Cl.
*A23L 33/00* (2016.01)

(52) U.S. Cl.
CPC .............. *A23L 33/30* (2016.08); *A23L 33/40* (2016.08); *A23V 2002/00* (2013.01)

(58) Field of Classification Search
None
See application file for complete search history.

(56) References Cited

U.S. PATENT DOCUMENTS

| | | | |
|---|---|---|---|
| 1,093,486 A * | 4/1914 | Scott | B68B 1/02 54/24 |
| 5,470,839 A | 11/1995 | Laughlin et al. | |
| 5,776,887 A | 7/1998 | Wilbert et al. | |
| 8,021,681 B2 | 9/2011 | Cincotta | |
| 8,142,809 B2 | 3/2012 | Gannon | |
| 8,211,700 B2 | 7/2012 | Longo | |
| 8,728,815 B2 | 5/2014 | Longo | |
| 8,821,915 B2 | 9/2014 | Cincotta | |
| 8,865,646 B2 | 10/2014 | Longo | |
| 9,237,761 B2 | 1/2016 | Longo et al. | |
| 9,386,790 B2 * | 7/2016 | Longo | A23L 33/115 |
| 10,433,576 B2 * | 10/2019 | Longo | A61P 3/08 |
| 2004/0081678 A1 | 4/2004 | Cincotta | |
| 2005/0031671 A1 | 2/2005 | Johnson | |
| 2008/0070826 A1 | 3/2008 | Selby, III | |
| 2010/0280123 A1 | 11/2010 | Karau et al. | |
| 2011/0118528 A1 * | 5/2011 | Longo | A61P 3/02 514/517 |
| 2011/0223192 A1 | 9/2011 | Gahler et al. | |
| 2012/0129783 A1 | 5/2012 | Cincotta | |
| 2013/0045215 A1 | 2/2013 | Longo et al. | |
| 2013/0316948 A1 | 11/2013 | Longo | |
| 2014/0112909 A1 | 4/2014 | Longo et al. | |
| 2014/0328863 A1 | 5/2014 | Longo | |
| 2014/0227373 A1 | 8/2014 | Longo et al. | |
| 2014/0342975 A1 | 11/2014 | Cincotta | |
| 2015/0133370 A1 | 5/2015 | Longo | |
| 2016/0331016 A1 | 11/2016 | Longo et al. | |
| 2017/0035093 A1 | 2/2017 | Longo et al. | |
| 2017/0035094 A1 | 2/2017 | Longo et al. | |

FOREIGN PATENT DOCUMENTS

| | | | |
|---|---|---|---|
| CN | 101175416 A | | 5/2008 |
| CN | 102892421 A | | 1/2013 |
| EP | 0768043 A2 | | 4/1997 |
| KR | 1020110135986 A | | 12/2011 |
| RU | 2147228 C1 | | 4/2000 |
| WO | 2004014362 | | 2/2004 |
| WO | 2006108008 A2 | | 10/2006 |
| WO | 2012/075679 A1 | | 6/2012 |
| WO | 2013010090 | | 1/2013 |

OTHER PUBLICATIONS

Brown et al. (The British Journal of Diabetes & Vascular Disease, 13(2):68-72, Mar. 1, 2013) (Year: 2013).*
Familydoctor.org (downloaded on May 13, 2023 from URL: <https://familydoctor.org/condition/insulin-resistance/#:~:text=Can%20insulin%20resistance%20be%20prevented,and%20eating%20a%20healthy%20diet>) (Year: 2023).*
Weinraub (The cabbage soup diet; Feb. 21, 1996; downloaded from URL< The Cabbage Soup Diet—The Washington Post>) (Year: 1996).*
Patent Examination Report 2 dated Aug. 27, 2021 for NZ Appn. No. 715431 filed Dec. 21, 2015, 7 pgs.
1st Office Action dated Jan. 25, 2021 for KR 10-2016-7002588, 13 pgs (including Eng Translation).
2nd Office Action dated Sep. 29, 2021 for KR 10-2016-7002588, 10 pgs (including Eng Translation).
First Office Action dtd Mar. 19, 2020 for Japanese Appn. No. 2019-030105 filed Feb. 22, 2019, 7 pgs (including Eng Translation).
Patent Examination Report 1 dated Feb. 1, 2021 for NZ Appn. No. 715431 filed Dec. 21, 2015, 7 pgs.

(Continued)

*Primary Examiner* — Sergio Coffa
(74) *Attorney, Agent, or Firm* — Brooks Kushman P.C.

(57) ABSTRACT

A method of alleviating symptoms of, or treating, pancreatic beta-cell damage in a subject includes a step of identifying a subject having pancreatic beta-cell damage. Multiple cycles of a diet protocol are administered to the subject. The diet protocol includes administering of a fasting mimicking diet and a re-feeding diet where the fasting mimicking diet is provided for a first time period and the re-feeding diet is provided for a second time period.

20 Claims, 15 Drawing Sheets

(56) References Cited

OTHER PUBLICATIONS

Belkacemi, L. et al., "Intermittent Fasting Modulation of the Diabetic Syndrome in Streptozotocin-Injected Rats," Int'l. Journal of Endocrinology, v. 2012, Article ID 962012, 2012, 12 pgs.
Brown, J.E. et al., "Intermittent fasting: a dietary intervention for prevention of diabetes and cardiovascular disease?", The British Journal of Diabetes and Vascular Disease, 13(2), 2013, pp. 68-72.
Chaudhry, Z.Z. et al., "Streptozotocin is equally diabetogenic whether adminstered to fed or fasted mice," Laboratory Animals 47(4), 2013, pp. 257-265.
Dulloo, A.G. et al., "Differential Effects of High-Fat Diets Varying in Fatty Acid Composition on the Efficiency of Lean and Fat Tissue Deposition During Weight Recovery After Low Food Intake," Metabolism, v. 44, n. 2 (Feb. 1995), pp. 273-279.
Halberg, N. et al., "Effect of intermittent fasting and refeeding on insulin action in healthy men," J. Appl. Physiol 99, 2005, pp. 2128-2136.
Hall, P., "Nutrition Watch. Intermittent energy restriction diets lead to greater insulin sensitivity and fat loss," Food Australia, 2013, 6 pgs.
Harvie, M. et al., "The effect of intermittent energy and carboyhydrate restriction v. daily energy restriction on weight loss and metabolic disease risk markers in overweight women," Br. J. Nutr. 2013, 110(8), pp. 1534-1547.
International Search Report dated Oct. 27, 2014 in PCT/US2014/045090 filed Jul. 1, 2014, 4 pgs.
Karbowska, J. et al., "Intermittent fasting up-regulates Fsp27/Cidec gene expression in white adipose tissue," Nutrition 28, 2012, pp. 294-299.
Lim, E.L. et al., "Reversal of type 2 diabetes: normalisation of beta cell function in association with decreased pancreas an liver triacylglyercol," Diabetologia (2011), 54:2506-2514.
Matschinsky, F.M. et al., "Adaptations of alpha- and beta-cells of Rat and Mouse Pancreatic Islets to Starvation, to Refeeding after Starvation, and to Obesity," J. Clin. Invest, v. 65, 1980, pp. 207-218.
Ono, et al., "An Attempt to Reduce the Body Weight in Highly Obese Patients (especially on the effects achieved by differences in saccharide contents)", Department of Nutritional Guidance, Oita Prefectural Hospital Medical Journal, v. 25, 1996, pp. 129-132 (English Abstract only).
Polak, D.J., Regenerative medicine. "Oportunities and Challenges a brief overview," J R Soc Interface, 2010, 7 Suppl 6, pp. 777-781.
Prevention, Merriam-Webster Online Dictionary [online], [retrieved Feb. 7, 2015], retrieved from the Internet <URL.
Pokrovskiy, M., "Encyclopedicheskiy slovar' medicynskih terminov," Medicina, 2001, p. 295.
Tommelmans, L., "The Challenge of Regenerative Medicine," Hastings Cent. Rep., 2010, 4(6), pp. 24-26.
Wier, G.C. et al., "Five Stages of Evolving Beta-Cell Dysfunction During Progression to Diabetes," Diabetes 53, Suppl. 3, pp. 16-21 (2004).
Examination Report dated Jan. 16, 2019 for Australian Appn. No. 2018200207, 7 pgs.
Woolworths Chargrilled Eggplant prepacked 180g downloaded on Jan. 10, 2019 from https://www.woolworths.com.au/shop/productdetails/505676/woolworths-chargrilled-eggplant-prepacked, 1 pg.
Yang, M.U. et al., "Composition of weight lost during short-term weight reduction. Metabolic responses of obese subjects to starvation and low-calorie ketogenic and nonketogenic diets," J. Clin. Invest., 58(3), 1976, pp. 722-730.
180 degrees Crackers Oat Walnut downloaded on Jan. 10, 2019 from https://www.woolworths.com.au/shop/productdetails/289839/180-degrees-oat-crackers-walnut, 3 pgs.
Lucky walnuts, cashews & almonds 6 pack downloaded on Mar. 1, 2019 from https://www.woolworths.com.au/shop/productdetails/208931/lucky-walnuts-cashews-almond, 3 pgs.
Black Swan Avacado dip downloaded Jan. 10, 2018 from https://shop.coles.com.au/a/a-national/product/black-swan-farmers-best-dip-salmon-avacado, 3 pgs.
$1^{st}$ Korean Office Action, $1^{st}$ New Zealand Office Action.
$2^{nd}$ Korean Office Action, $1^{st}$ New Zealand Office Action.
$1^{st}$ Japanese Office Action, $1^{st}$ New Zealand Office Action.
KR20110135986A, English Abstract and U.S. Equivalent U.S. Pub. No. 2010/0280123.
Hall, R., "Nutrition Watch: Intermittent energy restriction diets lead to greater insulin sensitivity and fat loss," Food Aust. v. 65, n. 3, 2013, pp. 36-39.
Reiko, O. et al., "Weight loss attempted by very low-calorie diets in severely obese subjects—particularly, the effects of different sugar contents," The Medical Journal of the Oita Prefectural Hospital, 1996, v. 25, pp. 129-132.
1st Office Action dated Jul. 26, 2022 for JP 2021-094925, 12 pgs (including Eng Translation).
Mning, E.P.G. et al., "A Multicenter Study of the Efficacy of the Ketogenic Diet," Arch Neurol (1988), v. 55, pp. 1433-1437.

\* cited by examiner

| Body Weight | Day1 | Day2 | Day3 | Day4 | Day5 | Δ5-day [1] | Δ5-day [2] |
|---|---|---|---|---|---|---|---|
| | *kcal/day* | | | | | | |
| ≥200 lbs | 1170 | 828 | 768 | 810 | 833 | -5591 | -9591 |
| 151-200 lbs | 1134 | 790 | 737 | 774 | 795 | -5772 | -7772 |
| ≤150 lbs | 1098 | 751 | 706 | 738 | 756 | -5952 | -5952 |
| | *kcal/lb* | | | | | | |
| 250 lbs | 4.7 | 3.3 | 3.1 | 3.2 | 3.3 | | |
| 200 lbs | 5.7 | 3.9 | 3.7 | 3.9 | 4.0 | | |
| 150 lbs | 7.3 | 5.0 | 4.7 | 4.9 | 5.0 | | |
| | *kcal/kg* | | | | | | |
| 113 kg | 10.3 | 7.3 | 6.8 | 7.1 | 7.3 | | |
| 91 kg | 12.5 | 8.7 | 8.1 | 8.5 | 8.8 | | |
| 68 kg | 16.1 | 11.0 | 10.4 | 10.8 | 11.1 | | |

[1] based on a 2,000 calorie per day diet
[2] based on 2,800, 2,400, and 2,000 calorie diets for person's weight ≥200, 150-200, and ≤150 lbs, respectively.

Table 1. The fasting mimicking diet (FMD), Prolon, was developed by the L-Nutra to induce a fasting-like response while maximizing nourishment.

*Fig. 1*

|  | Day 1 | Day 2,3,4,5 |
|---|---|---|
| Total Calorie | 1152 | 809 |
| Fat | 56% | 46% |
| Carbohydrate | 34% | 46% |
| Sugar | 10% | 9% |
| Protein | 10% | 9% |

Table 2. The macronutrient content for each day of the 5 day FMD regimen based on an average 180-200 lbs person.

Fig. 2

|  | Unit | Day 1 | % DV* | Day 2,3,4,5 | % DV* | Ave % DV* |
|---|---|---|---|---|---|---|
| Protein | g | 29 |  | 18 |  |  |
| Fat | g | 72 |  | 41 |  |  |
| Carb (by diff) | g | 98 |  | 91 |  |  |
| From Sugars | g | 29 |  | 17.6 |  |  |
| Dietary Fiber | g | 22 | 86% | 14 | 56% | 62% |
| Calcium | mg | 604 | 60% | 426 | 43% | 46% |
| Iron | mg | 13 | 77% | 10 | 55% | 60% |
| Magnesium | mg | 387 | 97% | 230 | 58% | 65% |
| Phosphorus | mg | 390 | 39% | 276 | 28% | 30% |
| Potassium (K) | mg | 2519 | 72% | 1795 | 51% | 55% |
| Sodium (Na) | mg | 2427 | 101% | 1750 | 73% | 79% |
| Zinc | mg | 7 | 46% | 4.2 | 28% | 32% |
| Copper | mg | 1.5 | 76% | 1.2 | 59% | 63% |
| Manganese | mg | 3 | 148% | 1.9 | 95% | 105% |
| Selenium | mcg | 7 | 10% | 5.3 | 8% | 8% |
| Vit A | IU | 39254 | 785% | 27549 | 551% | 598% |
| Vit C | mcg | 236 | 393% | 137 | 229% | 261% |
| Vit B1 Thiamin | mg | 4 | 209% | 2.2 | 113% | 132% |
| Vit B2 Riboflavin B2 | mg | 3.8 | 191% | 2 | 109% | 126% |
| Vit B3 Niacin | mg | 28.5 | 143% | 18 | 92% | 102% |
| Vit B5 Pantothenic Acid | mg | 1.2 | 12% | 1.0 | 10% | 10% |
| Vit B6 Pyridoxal phosphate | mg | 4.0 | 200% | 2.2 | 111% | 129% |
| Vit B9 Folate | mg | 479 | 120% | 317 | 79% | 87% |
| B12 Cobalamin | mcg | 16 | 227% | 16 | 227% | 227% |
| Vit D | IU | 952 | 238% | 952 | 238% | 238% |
| Vit E | mcg | 25 | 127% | 16 | 80% | 89% |
| Vit K | mg | 1795 | 2243% | 1110 | 1387% | 1559% |

Table 3. *The micronutrient content for each day of the 5 day FMD regimen based on an average 180- 200 lbs person.*

Fig. 3

FASTING CONDITION AS DIETARY TREATMENT OF DIABETES

CROSS REFERENCE TO RELATED APPLICATION

This application is a continuation of U.S. Ser. No. 16/592,299 filed Oct. 3, 2019, now U.S. Pat. No. 10,932,486 issued Mar. 2, 2021, which is a continuation of U.S. Ser. No. 15/204,156 filed Jul. 7, 2016, now U.S. Pat. No. 10,433,576 issued Oct. 8, 2019, which is a continuation of U.S. Ser. No. 14/320,996 filed Jul. 1, 2014, now U.S. Pat. No. 9,386,790 issued Jul. 12, 2016, which claims the benefit of U.S. provisional application Ser. No. 61/841,709 filed Jul. 1, 2013, the disclosures of which are incorporated in their entireties by reference herein.

STATEMENT REGARDING FEDERALLY SPONSORED RESEARCH OR DEVELOPMENT

This invention was made with government support under Grant Nos. AG034906 and AG020642, awarded by the National Institutes of Health. The government has certain rights in the invention.

TECHNICAL FIELD

The present invention, in general, relates to compositions and methods for a) regenerating pancreatic cells, 2) treating Type I diabetes, 3) treating Type II diabetes, 4) treating the metabolic syndrome, 5) preventing Type II diabetes and other diseases associated with metabolic syndrome. In particular, the present invention promotes pancreatic regeneration and alleviates multiple common signs, symptoms and risk factors of both diabetes types. In addition to promoting residential pancreatic regeneration, it can also be used to enhance and improve the regenerative functions of transplanted stem cells when it is incorporated with the conventional stem cell therapy.

BACKGROUND

Human metabolic disorders such as diabetes mellitus Type I, diabetes mellitus Type II, metabolic syndrome, and insulin resistance are serious health conditions affecting over a third of the adult population in the United States. Although effective in delaying morbidity, standard treatments have not generally been able to reverse the associated damage of these disorders.

Chemicals, cytokines/hormones and stem cell or islet transplantation that boost or assist pancreatic regeneration have been used as diabetes therapy in order to augment or replace insulin injections by increasing the number of, or enhancing the function of, endogenous insulin-producing β-cells.

Diabetes mellitus Type 1 and Type 2 diabetes are characterized by progressive beta-cell failure. By far, stem/progenitor cell transplantation is the only therapy available for advanced stages of diabetes in an attempt to restore insulin production and replace insulin injection. However, besides ethical issues, technical and safety challenges in stem cell isolation, maintenance, expansion, donor-recipient matching and transplantation limit the efficacy of these strategies.

Accordingly, there is a need for safe, effective treatment protocols for metabolic disorders such as diabetes that may reverse pancreatic damage and inhibit development of these disorders.

SUMMARY

In at least one embodiment, the present invention provides a method of alleviating symptoms of or treating pancreatic beta-cell damage in a subject. The method includes a step of identifying a subject having pancreatic beta-cell damage. Multiple cycles of a diet protocol are administered to the subject. The diet protocol includes administering of a fasting mimicking diet and a re-feeding diet where the fasting mimicking diet is provided for a first time period and the re-feeding diet is provided for a second time period.

In another embodiment, a method of alleviating symptoms of or treating pancreatic beta-cell damage in a subject is provided. The method includes a step of identifying a subject having pancreatic beta-cell damage and insulin defeciency. The subject's normal caloric intake is determined. Multiple cycles of a diet protocol are administered to the subject. The diet protocol includes administering of a fasting mimicking diet and a re-feeding diet where the fasting mimicking diet is provided for a first time period (e.g., 2 to 6 days) and the re-feeding diet is provided for a second time period (e.g., 7 to 85 days). The fasting mimicking diet provides less than about 50% of the normal caloric intake of the subject with both protein restriction and sugar restriction and the re-feeding provides 60-100 percent of the normal caloric intake of the subject, depending on the need to lose additional weight.

In another embodiment, a method of alleviating a symptom of diabetes is provided. The method includes a step of identifying a subject having diabetes (Type I or II). The subject is provided with multiple cycles of a Fasting Mimicking Diet (FMD) (4-5 days every, 1-12 weeks) to promote a reduction and reversal in symptoms.

In another embodiment, a method of alleviating insulin resistance, insulin deficiency and/or hyperglygemia is provided. The method includes a step of identifying a subject having insulin resistance, insulin defeceincy and/or fasting hyperglycemia diabetes. The subject is provided with multiple cycles of a Fasting Mimicking Diet (FMD) (e.g., 4-5 days every 4-12 weeks) to promote a reduction in symptoms.

In another embodiment, a method of alleviating a symptom of metabolic syndrome is provided. The method includes a step of identifying a subject having one or more metabolic syndrome symptoms/risk factors (e.g., high blood pressure, hyperglycemia, excess body fat around the waist, high cholesterol). The subject is provided with multiple cycles of a Fasting Mimicking Diet (FMD) (4-5 days every, 1-12 weeks) to promote a reduction in symptoms.

BRIEF DESCRIPTION OF THE DRAWINGS

FIG. 1. Table 1 showing the Calorie overview of the fasting mimicking diet adjusted to human subjects. The fasting mimicking diet (FMD), Prolon, induces a fasting-like response while maximizing nourishment. The consumed calories for each one of the 5 days of the diet are shown, as well as the adjusted kcal per pound and kilogram of body weight. The reduction in calories consumed during the 5 day dietary regimen (Δ5-day) is shown as either 1) based on a 2,000 calorie per day diet, or 2) based on 2,800, 2,400, and 2,000 calorie diets for person's weight ≥200, 150-200, and ≤150 lbs, respectively;

FIG. 2. Table 2 showing the defined macronutrient content for each diet day adjusted to a 180-200 lbs human subject. The macronutrient content for each day of the 5 day FMD regimen is based on an average 180-200 lbs person. Caloric intake on day 1 of the diet is less reduced compared to the following days (2-5) to allow the body to adjust to the low calorie consumption. % of calories contributed by fat, carbohydrate (by sugar in detail) and protein for each day of the Prolon regimen is presented.

FIG. 3. Table 3 showing the defined micronutrient content for each diet day adjusted to a 180-200 lbs human subject in a variation of the invention. The micronutrient content for each day of the 5 day FMD regimen based on an average 180-200 lbs person. Percent of the daily value (% DV) is calculated based on a 2,000 calorie diet. * for some of the micronutrients, DV is not defined; values shown are based on the reference daily intake (RDI).

DETAILED DESCRIPTION

Figure 4A:
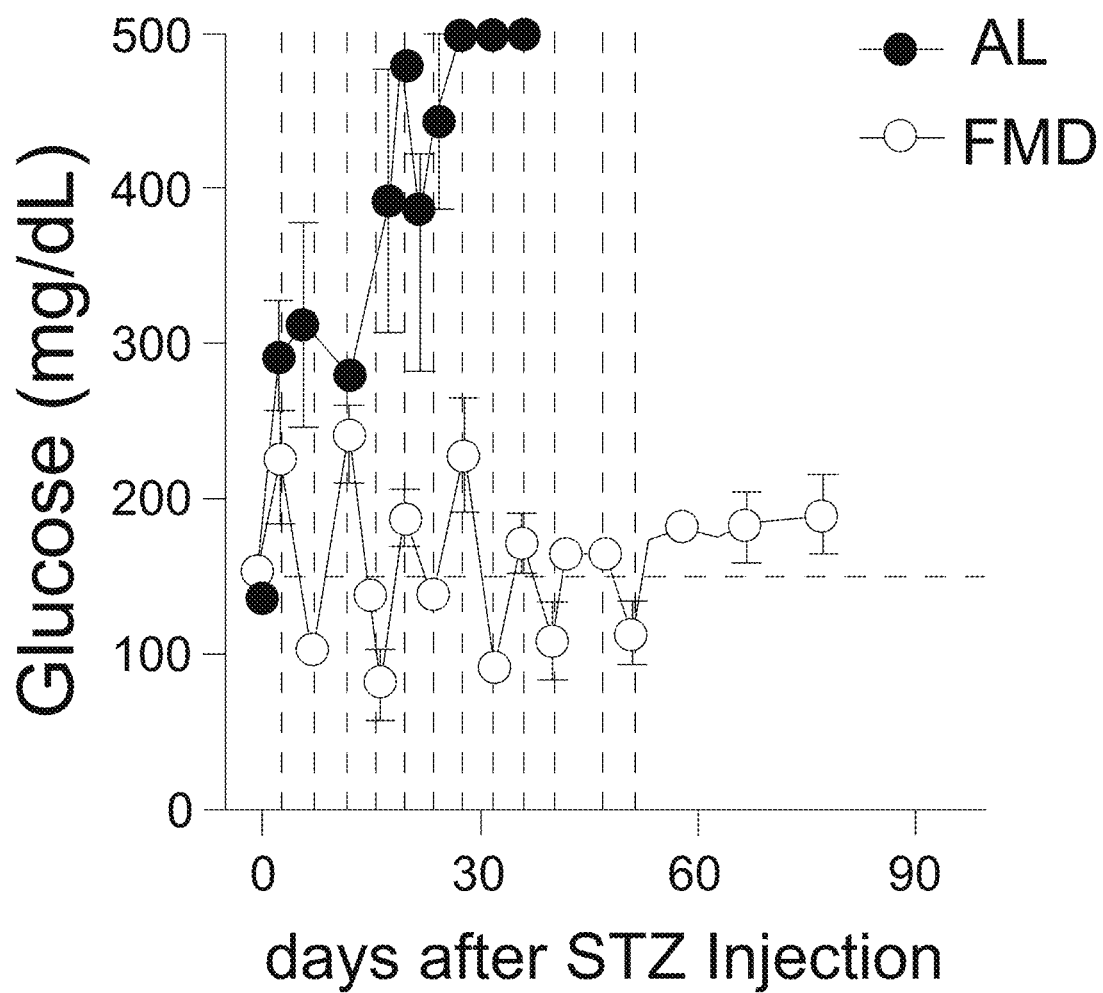
FIGS. 4A, 4B, 4C, 4D, and 4E. Fasting mimicking diet (FMD, as described in FMD1 and FMD2 sections) in Type I diabetes mice. (A) Blood glucose levels of mice with STZ-induced hyperglycemia. Vertical dash lines indicate the cycles of FMD. Horizontal dash line indicates the level of blood glucose in healthy controls. (B) Plasma insulin levels of STZ-treated mice with or without FMD. Horizontal dash line indicates the level of plasma insulin in healthy controls (1.81±0.25 ug/L). (C) Glucose tolerance and Insulin tolerance test. Mice were injected with glucose or insulin and the blood glucose levels were measured over a 60 min period. (D) Immunofluorescence staining of pancreatic islets for insulin (bright area). In FMD group, both rescued (euglycemic) and unrescued (pre-hyperglycemic) mice contained more insulin-secreting beta-cells comparing to the AL group. (E) Survival curve of STZ treated mice.

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

The terms "kilocalorie" (kcal) and "Calorie" refer to the food calorie. The term "calorie" refers to the so-called small calorie.

The term "subject" refers to a human or animal, including all mammals such as primates (particularly higher primates), sheep, dog, rodents (e.g., mouse or rat), guinea pig, goat, pig, cat, rabbit, and cow.

The term "metabolic syndrome" as used herein means a disorder that increases a subject's risk of cardiovascular disease, stroke, and Type II diabetes. The syndrome includes the following metabolic risks factors: a large waistline, high blood pressure, low high density lipoprotein (HDL) levels (<40 mg/dL), and high fasting glucose levels (or a subject on medication to treat high glucose levels). Typically, a subject having three or more of these risk factors is classified as having metabolic syndrome.

The term "fasting glucose level" means the glucose level in the blood of a subject after 8 hours of fasting. In human subjects, the normal fasting glucose blood level is less than 100 mg/dL (e.g. 70 to 99 mg/dL).

Abbreviations

"STZ" is Streptozotocin.
"FMD" is fasting mimicking diet.
"AL" is ad libitum.

In an embodiment, a method of alleviating symptoms of or treating pancreatic beta-cell damage in a subject is provided. In this context, pancreatic beta-cell damage includes beta cell loss, beta cell dysfunction, or combinations thereof. In variations of the present embodiment, the method is used to treat or alleviate one or more symptoms of diabetes mellitus Type I, diabetes mellitus Type II, metabolic syndrome, and insulin resistance. The method includes a step of identifying a subject having pancreatic beta-cell damage. The subject's normal caloric intake is typically determined by interrogation or from the subject's weight. Multiple cycles of a diet protocol are administered to the subject. The diet protocol includes administering of a fasting mimicking diet and a re-feeding diet where the fasting mimicking diet is provided for a first time period and the re-feeding diet is provided for a second time period.

The fasting mimicking diet provides the subject with less than about 50% of the normal caloric intake of the subject. In a variation the fasting mimicking diet is provided with protein restriction and/or carbohydrate restriction and/or sugar restriction. In one useful refinement, the re-feeding provides 60-100 percent of the normal caloric intake of the subject. In a refinement, the fasting mimicking diet provides the subject with at most, in increasing order of preference, 60%, 50%, 45%, 40%, or 35% of the normal caloric intake of the subject with both protein restriction and carbohydrate/sugar restriction and at least, in increasing order of preference, 0%, 5%, 10%, or 15% of the normal caloric intake of the subject with both protein restriction and sugar restriction. The re-feeding provides the subject with at least 60 percent of the normal caloric intake of the subject. In a refinement, the re-feeding diet provides the subject with at least, in order of preference, 60%, 70%, 80%, 90%, or 100% of the normal caloric intake of the subject and at most, in order of preference, 130%, 120%, 110%, or 105% of the normal caloric intake of the subject. In a variation, the re-feeding diet provides an amount of calories that depends on the need of the subject to lose weight. For example, a subject needing weight reduction can be provided a re-feeding diet that provides from 60 to 90 percent of their normal caloric intake. In a refinement, a subject needing weight reduction can be provided a re-feeding diet that provides from 60 to 80 percent of their normal caloric intake. In another refinement, a subject needing weight reduction can be provided a re-feeding diet that provides from 60 to 70 percent of their normal caloric intake. Subject not requiring weight loss can be provided with from 90 to 130 percent of their normal caloric intake during the re-feeding diet phase.

In a variation, the fasting mimicking diet provides the subject with 4.5 to 7 kcal/pound of body weight/day on day 1 followed by 3 to 5 kcal kcal/pound of body weight/day for days 2 to 5. In a refinement, the fasting mimicking diet provides the subject with 7 kcal/pound of body weight/day on day 1 followed by 4 kcal kcal/pound of body weight/day for days 2-5. In another variation, the fasting mimicking diet provides the subject with 3-6 kcal/pound of body weight/day on day 1 followed by 2-4 kcal kcal/pound of body weight/day for days 2-4. In some variations, the fasting mimicking diet includes 2 to 5% calories from glycerol. For example, the fasting mimicking diet can include at least 60% calories from fatty acids, 2-5% calories from glycerol and up to 5% of calories from plant-based proteins, and a maximum of 35% of calories from carbohydrates. Advantageously, the carbohydrates are complex carbohydrate from plant sources such as soy, rice, or other grains and at least 50% of the calories from fatty acids are from coconut oil and tree nuts (e.g., macadamia nuts, walnuts, or almonds).

Typical fat sources include vegetable oil such as soybean oil. In a further refinement, the low protein diet incudes fat sources such that at least 25 percent of calories from fat are short-chain fatty acids having from 2 to 7 carbon atoms and/or from medium-chain saturated fatty acids having from 8 to 12 carbon atoms. Specific examples of fatty acids include lauric and/or myristic acid and fat sources include olive oil, kernel oil and/or coconut oil. In another refinement, the fasting mimicking diet includes calories from fat in an amount from about 0 to 22 percent of total calories contained in the diet.

U.S. patent application Ser. No. 14/178,953 filed on Feb. 12, 2014 provides examples of fasting mimicking diets that are useful in the methods of the present invention. In this regard, FIGS. 1-3 provide listings of the nutrients for day one through day five. In addition to the macronutrients, the diet should contain less than 30 g of sugar on day 1 and less than 20 g of sugar on days 2-5. The diet should contain less than 28 g of proteins on day 1 and less than 18 g of proteins on days 2-5, mostly or completely from plant based sources. The diet should contain between 20 and 30 grams of monounsaturated fats on day 1 and 10-15 grams of mono-unsaturated fats on days 2-5. The diet should contain between 6 and 10 grams of polyunsaturated fats on day 1 and 3-5 grams of polyunsaturated fats on days 2-5. The diet should contain less than 12 g of saturated fats on day 1 and less than 6 grams of saturated fats on days 2-5. Typically, the fats on all days are derived from a combination of the following: Almonds, Macadamia Nuts, Pecans, Coconut, Coconut oil, Olive Oil and Flaxseed. In a refinement, the FMD diet includes over 50% of the recommended daily value of dietary fiber on all days. In the further refinement, the amount of dietary fiber is greater than 15 grams per day on all five days. The diet should contain 12-25 grams of glycerol per day on days 2-5. In a refinement, glycerol is provided at 0.1 grams per pound body weight/day. In a variation, the FMD includes the following micronutrients (at least 95% non-animal based): over 5,000 IU of vitamin A per day (days 1-5); 60-240 mg of vitamin C per day (days 1-5); 400-800 mg of Calcium per day (days 1-5); 7.2-14.4 mg of Iron per day (days 1-5); 200-400 mg of Magnesium per day (days 1-5); 1-2 mg of copper per day (days 1-5); 1-2 mg of Manganese per day (days 1-5); 3.5-7 mcg of Selenium per day (days 1-5); 2-4 mg of Vitamin B1 per day (days 1-5); 2-4 mg of Vitamin B2 per day (days 1-5); 20-30 mg of Vitamin B3 per day (days 1-5); 1-1.5 mg of Vitamin B5 per day (days 1-5); 2-4 mg of Vitamin B6 per day (days 1-5); 240-480 mcg of Vitamin B9 per day (days 1-5); 600-1000 IU of Vitamin D per day (days 1-5); 14-30 mg of Vitamin E per day (days 1-5); over 80 mcg of Vitamin K per day (days 1-5); 16-25 mcg Vitamin B12 are provided during the entire 5-day period; 600 mg of Docosahexaenoic acid (DHA, algae-derived) are provided during the entire 5-day period. The FMD diet provides high micronutrient content mostly (i.e., greater than 50 percent by weight) from natural sources including: Kale, Cashews, Yellow Bell Pepper, Onion, Lemon Juice, Yeast, Turmeric. Mushroom, Carrot, Olive Oil, Beet Juice, Spinach, Tomato, Collard, Nettle, Thyme, Salt, Pepper, Vitamin B12 (Cyanocobalamin), Beets, Butternut Squash, Oregano, Tomato Juice, Orange Juice, Celery, Romaine Lettuce, Cumin, Orange Rind, Citric Acid, Nutmeg, Cloves, and combinations thereof. Table 4 provides an example of additional micronutrient supplementation that can be provided in the FMD diet:

TABLE 4

Micronutrient Supplementation

| | Supplement | Formula | Amount | Amount Range | Unit |
|---|---|---|---|---|---|
| Vit A | | | 1250 IU | 900-1600 | IU |
| Vit C | Ascorbic Acid | $C_6H_8O_6$ | 15.0000 | 10-20 | mg |
| Ca | Calcium Carbonate | $CaCO_3$ | 80.0000 | 60-100 | mg |
| Fe | Ferrous Fumarate | $C_4H_2FeO_4$ | 4.5000 | 3-6 | mg |
| Vit D3 | Cholecalciferol | $C_{27}H_{44}O$ | 0.0025 | 0.001-0.005 | mg |
| Vit E | dl-Alpha Tocopheryl Acetate | $C_{29}H_{50}O_2$ | 5.0000 | 3-7 | mg |
| Vit K | Phytonadione | | 0.0200 | 0.1-0.04 | mg |
| Vit B1 | Thiamine Mononitrate | $C_{12}H_{17}N_5O_4S$ | 0.3750 | 0.15-0.5 | mg |
| Vit B2 | Riboflavin E101 | $C_{17}H_{20}N_4O_6$ | 0.4250 | 0.2-0.6 | mg |
| Vit B3 | Niacinamide | $C_6H_6N_2O$ | 5.0000 | 3-7 | mg |
| Vit B5 | Calcium Pantothenate | $C_8H_{32}CaN_2O_{10}$ | 2.5000 | 1.5-4.0 | mg |
| Vit B6 | Pyridoxine Hydrochloride | $C_8H_{11}NO_3 \cdot HCl$ | 0.5000 | 0.3-0.7 | mg |

TABLE 4-continued

Micronutrient Supplementation

| | Supplement | Formula | Amount | Amount Range | Unit |
|---|---|---|---|---|---|
| Vit B7 | Biotin | $C_{10}H_{16}N_2O_3S$ | 0.0150 | 0.01-0.02 | mg |
| Vit B9 | Folic Acid | $C_{19}H_{19}N_7O_6$ | 0.1000 | 0.07-0.14 | mg |
| Vit B12 | Cyanocobalamin | $C_{63}H_{88}CoN_{14}O_{14}P$ | 0.0015 | 0.001-0.002 | mg |
| Cr | Chromium Picolinate | Cr(C6H4NO2)3 | 0.0174 | 0.014-0.022 | mg |
| Cu | Cupric Sulfate | $CuSO4$ | 0.2500 | 0.18-0.32 | mg |
| I | Potassium Iodide | KI | 0.0375 | 0.03-0.045 | mg |
| Mg | Magnesium Oxide | MgO | 26.0000 | 20-32 | mg |
| Mn | Manganese Sulfate | $MnSO_4$ | 0.5000 | 0.3-0.7 | mg |
| Mo | Sodium Molybdate | $Na_2MoO_4$ | 0.0188 | 0.014-0.023 | mg |
| Se | Sodium Selenate | $Na_2O_4Se$ | 0.0175 | 0.014-0.023 | mg |
| Zn | Zinc Oxide | ZnO | 3.7500 | 3-5 | mg |

In a variation as set forth above, the fasting mimicking diet also includes caloric restriction with respect to proteins and sugars (e.g., glucose). In one refinement, the fasting mimicking diet includes protein in an amount that is less than 15 percent of total calories provided by the fasting mimicking diet. In a further refinement, the fasting mimicking diet includes protein in an amount that is at most, in increasing order of preference, 15%, 12%, 10%, 8%, or 5% of total calories provided by the fasting mimicking diet and in an amount that is at least 0%, 2%, 3%, 5%, or 6% of total calories provided by the fasting mimicking diet. In another refinement, the fasting mimicking diet includes sugars in an amount that is less than 15 percent of total calories provided by the fasting mimicking diet. In a further refinement, the fasting mimicking diet includes sugars (e.g., glucose) in an amount that is at most, in increasing order of preference, 15%, 12%, 10%, 8%, or 5% of total calories provided by the fasting mimicking diet and in an amount that is at least, in order of preference, 0%, 2%, 3%, 5%, or 6% of total calories provided by the fasting mimicking diet.

The first time period during which the fasting mimicking diet is provided is typically from 2 to 6 days and the second time period during which the re-feeding diet is provide is typically 7 to 85 days. In a variation, the multiple cycles are administered once a month for at least 3 months. In a refinement, the first time period during which the fasting mimicking diet is provided for is, in increasing order of preference, 2, 7, 3, 6, 4, or 5 days. In another refinement, the second time period during which the re-feeding diet is provided is from, in increasing order of preference, 1 to 6 weeks, 1 to 5 weeks, 1 to 4 weeks, 1 to 3 weeks, or 1 to 2 weeks. The multiple cycles of the diet protocol may continue indefinitely. Advantageously, the multiple cycles of the diet protocol lasts for at least 60 days. In a refinement, the multiple cycles of the diet protocol lasts for at least, in order of preference, 30 days, 60 days, 90 days, 120 days, 180 days, 270 days, 1 year, 2 years, 5 years, or for the lifetime of the subject.

Surprisingly, the method and FMD of the present embodiment is found to induce pancreas and beta cell regeneration. This aspect of the invention is useful in treating subjects exhibiting both insulin resistance and the need for new beta cells (e.g., late stage type 2 diabetes) and subjects needing beta cell regeneration but do not have insulin resistance (e.g., type 1 diabetics). In another aspect, the method and FMD is found to increase the insulin sensitizer adiponectin, promote the loss of abdominal fat and cause insulin sensitization and a decrease in fasting glucose levels. Advantageously, the ability of the diet to reverse insulin resistance is useful in preventing the development of diabetes Type II in subjects exhibiting insulin resistance and/or fasting hyperglycemia but not having a diagnosis of diabetes. However, the diet is also useful for a normal subject who may be at risk of developing insulin resistance, metabolic syndrome or diabetes for any reason including excess adiposity, poor diet, genetic risk factors for diabetes etc.

Cycles of the fasting FMD a) promote insulin producing (3-cells regeneration, b) prevents and reverses severe hyperglycemia (>300 mg/dl) in both Type I and Type II diabetes in mammals (mice) and c) alleviates other complications of diabetes including insulin secretion deficiency, glucose tolerance impairment and insulin insensitivity. It also decreases fasting blood glucose levels in a pre-diabetic human subject, and it increases the insulin sensitizer adiponectin and the pancreatic regeneration factor betatrophin in humans confirming that this efficacy is conserved in mice and humans. This high efficiency diet protocol has broad effects on multiple complications of diabetes, low initial requirements and long-term safety/benefits allowing this invention to be practically incorporated with various types of therapy, including other conventional regenerative approaches as well as standard treatments of diabetes (under physician supervision) in a way that directly stimulates the resident stem cells and/or may indirectly change the microenvironments for promoting the regeneration of the transplanted stem cells in the recipients. The pancreatic regeneration caused by the FMD is only part of its effects on Types 1 and 2 diabetes. In fact, the FMD causes a reduction in glucose, reduction in IGF-I, decrease in insulin and an increase in insulin sensitivity, all of which are independent or partly independent of regeneration and contribute to the antidiabetes effects. In a refinement, the subject's levels of glucose, IGF-I, insulin and insulin sensitivity are measured to verify the correct changes.

In another embodiment, a method of alleviating a symptom of diabetes is provided. The method includes a step of identifying a subject suffering from diabetes (Types I or II). The subject is provided with multiple cycles of a Fasting Mimicking Diet (FMD) (4-5 days every, 1-12 weeks depending on severity of symptoms and levels of risk factors) to promote a reduction in symptoms. Cycles of the fasting FMD a) promote insulin producing (3-cells regeneration, b) prevents and reverses severe hyperglycemia (>300 mg/dl) in both Type I and Type II diabetes in mammals (mice) and c) alleviates other complications of diabetes including insulin secretion deficiency, glucose tolerance impairment and insulin insensitivity. It also decreases fasting blood glucose levels in a pre-diabetic human subject, confirming that this efficacy is conserved in mice and humans. It also decreases abdominal fat and increases the levels of the insulin sensitizer adiponectin. This high efficiency diet protocol has broad effects on multiple complications of diabetes, low initial requirements and long-term safety/benefits allowing this invention to be practically incorporated with various types of therapy, including other conventional regenerative approaches as well as standard treatments of diabetes (under physician supervision) in a way that directly stimulates the resident stem cells and/or may indirectly change the microenvironments for promoting the regeneration of the transplanted stem cells in the recipients. The pancreatic regeneration caused by the FMD is only part of its effects on Types 1 and 2 diabetes. In fact, the FMD causes a reduction in glucose, reduction in IGF-I, decrease in insulin and an increase in insulin sensitivity, all of which are independent or partly independent of regeneration and contribute to the anti-diabetes effects. In a refinement, the subject's levels of glucose, IGF-I, insulin and insulin sensitivity are measured to verify the correct changes.

Treatment and Prevention of Type 1 Diabetes.

Subjects with pancreatic beta-cell damage leading to partial or full Type I diabetes undergo multiple cycles of the FMD 1 or 2 diets as described herein. The number of cycles will depend on the severity of the disease and on the effect of each cycle of the FMD on beta cell regeneration and insulin production. The FMD will substitute a subject's normal diet for a period of 4-5 days every 1-4 weeks depending on the type and severity of the diabetes and insulin resistance, with the more frequent FMD prescribed to subjects with a more severe form of Type 1 diabetes. The frequency of the diet will also depend on the ability of subjects to return to within 5% of the normal weight before starting the next cycle of the diet and on the amelioration of the diabetes symptoms, with discontinuation or major reduction of the cycles once the values of insulin and glucose return to the normal range. For morbidly obese subjects, the FMD could be applied every 2 weeks for 5 days. The diet consists of ingredients which are Generally Regarded As Safe (GRAS) (see below). Because of the combination of potent immunomodulatory and anti-inflammatory effects, the FMD regimen described above can also be used to prevent the progression of Type 1 diabetes.

Treatment of Type 2 Diabetes.

Subjects with insulin resistance and/or pancreatic beta-cell damage leading to partial of full Type II diabetes will be asked to undergo multiple cycles of the FMD diet as described herein. The number and frequency of cycles can be determined by the physician depending on the severity of the disease and on the effect of each cycle of the FMD on insulin resistance, glucose tolerance, beta cell regeneration and insulin production and on the ability of the subject to maintain these improvements. Depending on the stage of the diabetes, insulin production may not be affected. The FMD will substitute a subject's normal diet for a period of 4-5 days every 1-12 weeks depending on the type and severity of the diabetes and insulin resistance, with the more frequent FMD prescribed to subjects with a more severe form of Type 2 diabetes, higher insulin resistance and body mass index. For subject within a normal BMI (<25), the frequency of the diet will also depend on the ability of subjects to return to within 5% of the normal weight before starting the next cycle of the diet. For overweight and obese subjects, the FMD could be applied as frequently as every week, based on the assessment of the physician. The diet consists of ingredients, which are Generally Regarded As Safe (GRAS) (see below).

FMD 1 (5 days): a low protein and low carbohydrate diet containing no or minimal animal derived components. The diet provides 7 kcal/pound of body weight for day 1 followed by 4 kcal/pound of body weight/day for days 2-5. At least 60% of calories are from a composition of fatty acids, preferably 100% from plant sources (with 50% or more coming from coconut oil and nuts including macadamia, walnuts, almonds), glycerol (2-5% of kcal) and 5% of calories from plant-based proteins (soy, rice, other grains)+a maximum of 35% of calories from carbohydrates mostly complex from plant sources. The diet is also high nourishment and provides, on each day, 30-50% of the daily recommended intake for all vitamins and minerals+essential fatty acids, with at least 50% of them coming from natural sources.

FMD 2 (4 days): a low protein and low carbohydrate diet containing no or minimal animal derived components. The diet provides 3-5 kcal/pound of body weight for day 1 followed by 2-4 kcal/pound of body weight/day for days 2-4. At least 60% of calories are from a composition of fatty acids (with 50% or more coming from coconut oil and nuts including macadamia, walnuts, almonds), glycerol (2-5% of kcal) and 5% of calories from plant-based proteins (soy, rice, other grains)+a maximum of 35% of calories from carbohydrates, mostly complex, from plant sources. The diet is also high nourishment and provides, on each day, 30-50% of the daily recommended intake for all vitamins and minerals+essential fatty acids, with at least 50% of them coming from natural sources.

In another embodiment, a method of alleviating or preventing insulin resistance and/or hyperglycemia is provided. The method includes a step of identifying a subject having insulin resistance and/or fasting hyperglycemia diabetes. In this regard, subjects having a family history of, or showing trending towards, insulin resistance and/or fasting hyperglycemia diabetes can also be treated to inhibit the development of these conditions. Indications of a subject trending towards insulin resistance and/or hyperglygemia include increasing weight, increasing fasting glucose levels, increasing hyperglycemia, increasing insulin resistance, and the like over several months to years (e.g., 6 months to 5 years). The subject is provided with multiple cycles of the fasting mimicking diet as set forth above for treating beta-cell damage and diabetes. In one particular variation, the FMD is provided to such subjects for 4-5 days every 4-12 weeks to promote a reduction in symptoms.

In another embodiment, a method of alleviating a symptom of or preventing metabolic syndrome is provided. The method includes a step of identifying a subject having one or more metabolic syndrome symptoms/risk factors. Examples of such symptoms/risk factors include high blood pressure, hyperglycemia, excess body fat around the waist, high total cholesterol, low HDL, and the like. In this regard, subjects having a family history of or showing trending towards metabolic syndrome can also be treated to inhibit the development of these conditions. Indications of a subject trending towards metabolic syndrome include a decreasing HDL, increasing total cholesterol, increasing weight, increasing fasting glucose levels, increasing hyperglycemia, increasing insulin resistance, and the like over several months to years (e.g., 6 months to 5 years). The subject is provided with multiple cycles of a Fasting Mimicking Diet (FMD) as set forth above for the treatment of beta-cell damage and diabetes. In one particular variation, the subject is provided with the FMD 4-5 days every 1-12 weeks to promote a reduction in symptoms.

In another embodiment, a diet package for implementing the fasting mimicking diets set forth above is provided. In general, the diet package includes rations for implementing the fasting mimicking diets set forth above. The sources of these rations are also set forth above. In particular, the rations are divided in portions for each cycle of the fasting mimicking diet. Alternatively, the rations are divided into portions for each day of the fasting mimicking diet. In another variation, the rations are divided into portions for each meal of the fasting mimicking diet. For example, the diet package includes a first set of rations for a fasting mimicking diet to be administered for the first time period to a subject, the fasting mimicking diet providing from 4.5 to 7 kilocalories per pound of subject for a first day and 3 to 5 kilocalories per pound of subject per day for a second to fifth day of the low protein diet. The diet package includes rations that provide less than 30 g of sugar on the first day; less than 20 g of sugar on the second to fifth days; less than 28 g of proteins on the first day; less than 18 g of proteins on the second to fifth days; 20 to 30 grams of monounsaturated fats on the first day; 10 to 15 grams of monounsaturated fats on the second to fifth days; between 6 and 10 grams of polyunsaturated fats on the first day; 3 to 5 grams of polyunsaturated fats on the second to fifth days; less than 12 g of saturated fats on the first day; less than 6 grams of saturated fats on the second to fifth days; and 12 to 25 grams of glycerol per day on the second to fifth days. In a refinement, the diet package further includes sufficient rations to provide the micronutrients set forth above. In a further refinement, the diet package provides instructions providing details of the methods set forth above.

The substitution diets are scaled for mice in the experiments set forth below to obtain equivalent changes in IGF-I (over 30% reduction), IGFBP1 (over 5 fold increase), ketone bodies (detection of high levels of B hydroxyl butyrate), glucose (at least 20% reduction) and insulin (at least 20% reduction). The FMD can be given as cycles of a preventive or therapeutic diet, every 1-12 weeks (see above) followed by a normal diet. Subsequent cycles must be postponed until the subject returns to a BMI of at least 18 or what is considered by the physician to be a healthy weight.

The following examples illustrate the various embodiments of the present invention. Those skilled in the art will recognize many variations that are within the spirit of the present invention and scope of the claims.

Mouse FMD Experiments

Figure 4B:
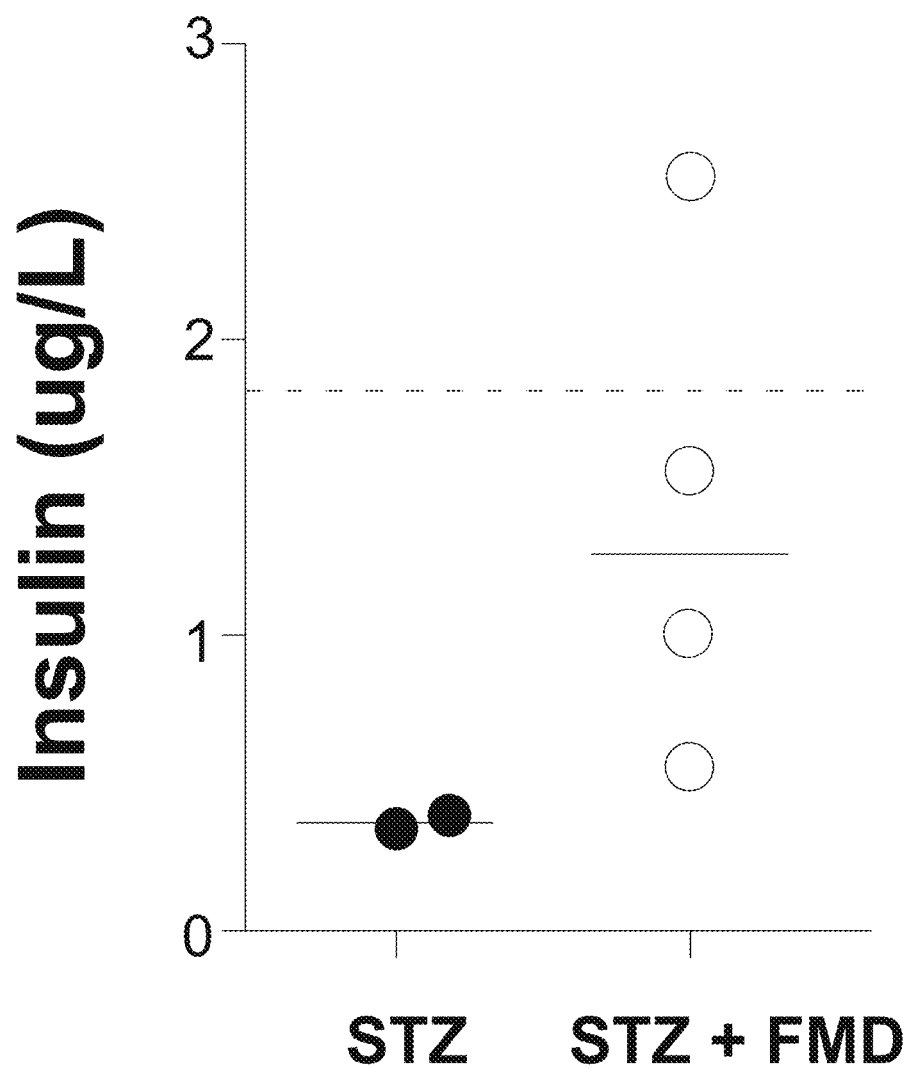
Figure 4C:
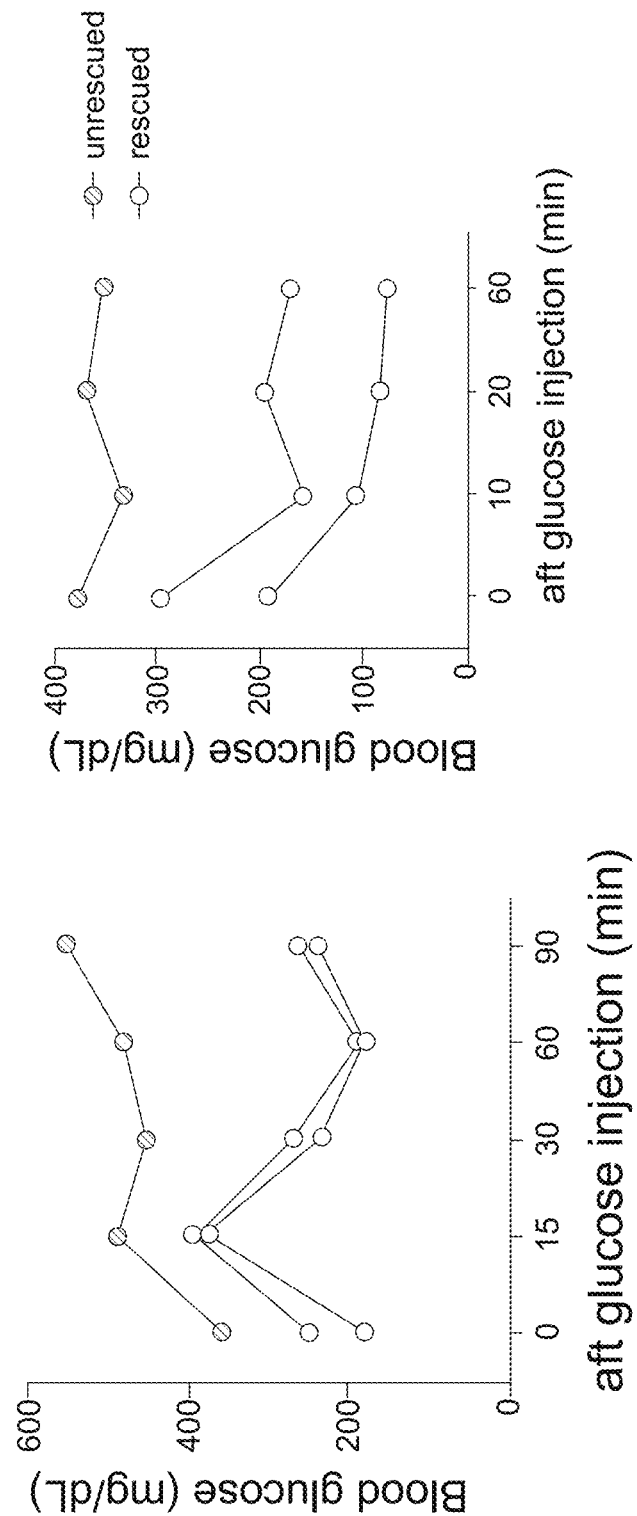
Figure 4D:
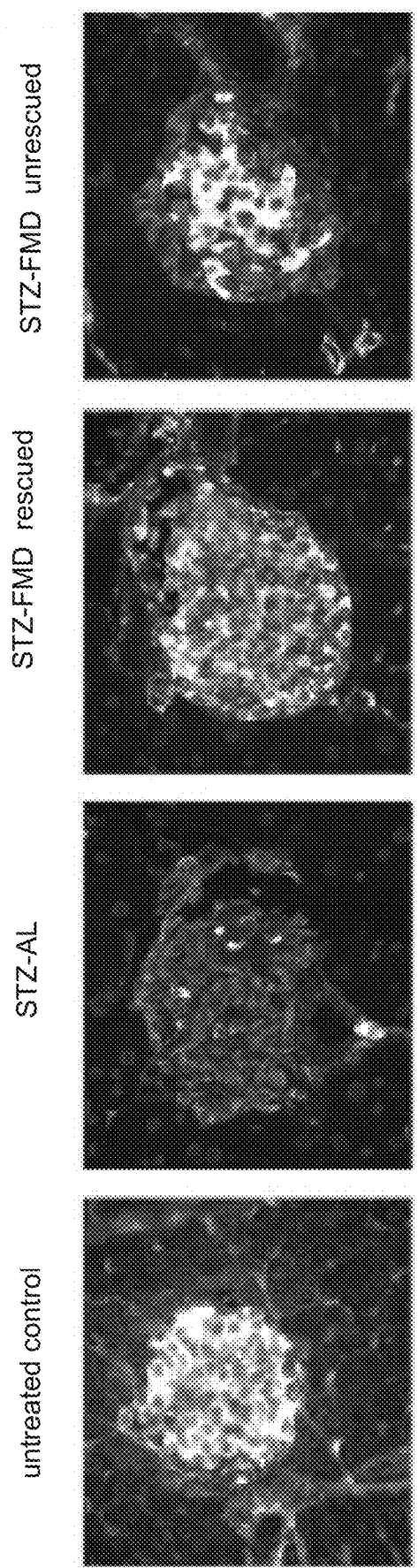
Figure 4E:
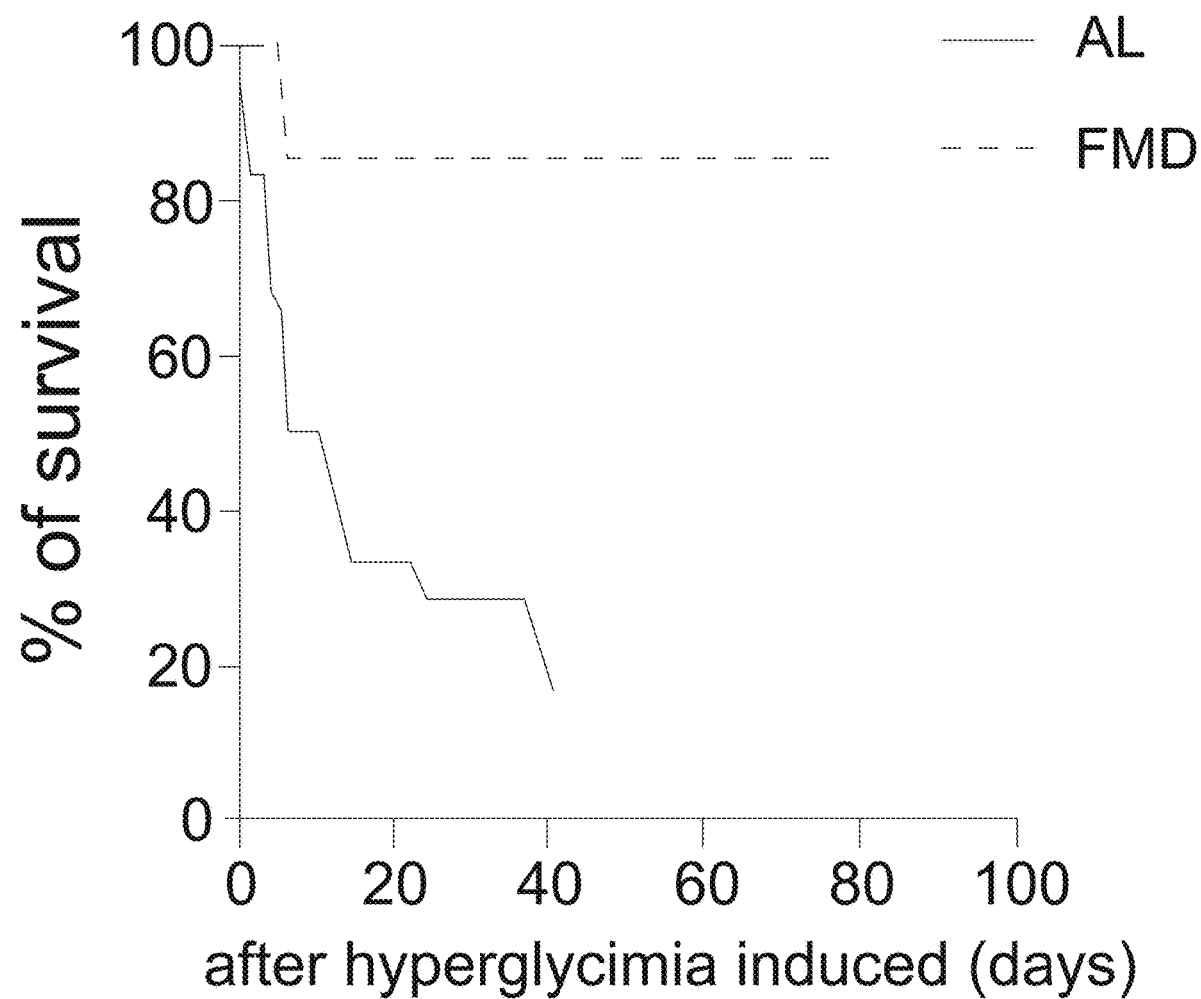

FIGS. 4A-E provide the results of the fasting mimicking diet (FMD) in Type I diabetes mice as described in FMD1 and FMD2 sections set forth above. FIG. 4A provides blood glucose levels of mice with STZ-induced hyperglycemia. The vertical dash lines indicate the cycles of FMD while the horizontal dash line indicates the level of blood glucose in healthy controls. FIG. 4B provides plasma insulin levels of STZ-treated mice with or without FMD. FIG. 4C provides glucose tolerance and insulin tolerance test results. Mice were injected with glucose or insulin and the blood glucose levels were measured over a 60 min period. FIG. 4D provides immunostaining of pancreatic islets for insulin (bright area). In the FMD group, both rescued and unrescued mice contained more insulin-secreting beta-cells comparing to the AL group. Finally, FIG. 4E provides a survival curve of STZ treated mice.

Figure 5A:
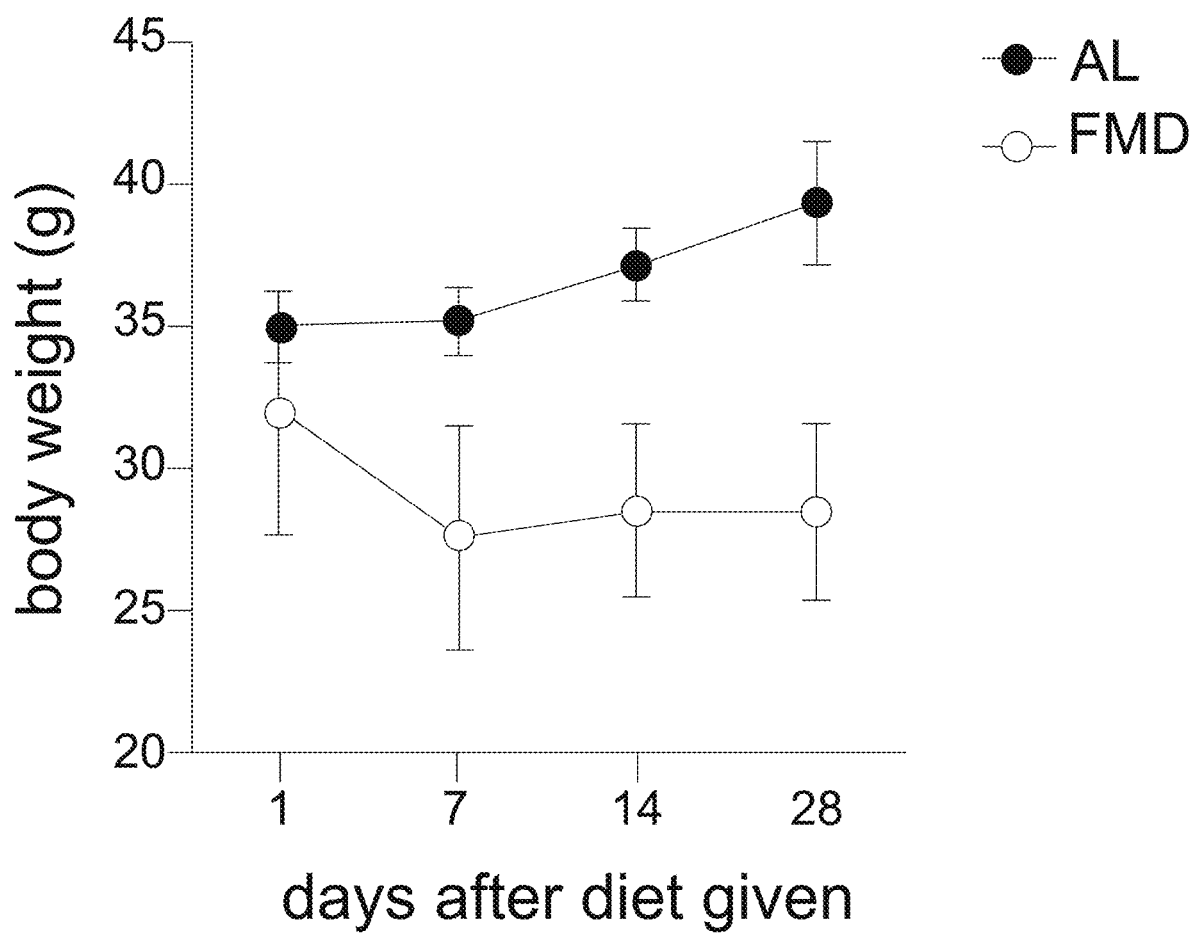
FIGS. 5A and 5B. Fasting mimicking diet (FMD as described in FMD1 and FMD2 sections) in Type II diabetes mice (lepr$^{db/db}$). (A) Body weight and (B) blood glucose level of db/db mice. 8-wks-old db/db mice were fed ad libitum or FMD. Vertical dash lines indicate the cycles of FMD.
Figure 5B:
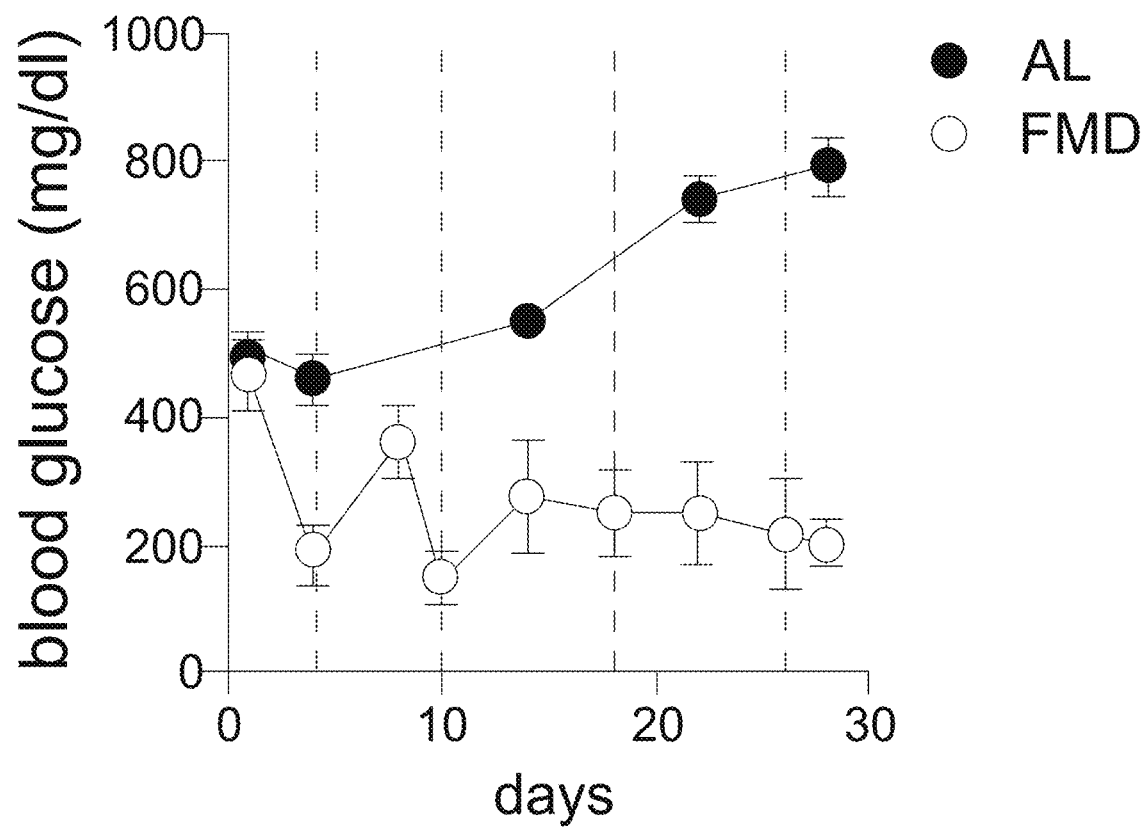

FIGS. 5A-B provide the results of the fasting mimicking diet in Type II diabetes mice (lepr$^{db/db}$) (as described in FMD1 and FMD2 sections). FIG. 5A provides the body weight while FIG. 5B provides the blood glucose level of db/db mice. In these experiments, 8-wks-old db/db mice were fed ad libitum or FMD. Vertical dash lines indicate the cycles of FMD, while the horizontal dash line indicates the blood glucose levels of non-diabetic controls.

Figure 6:
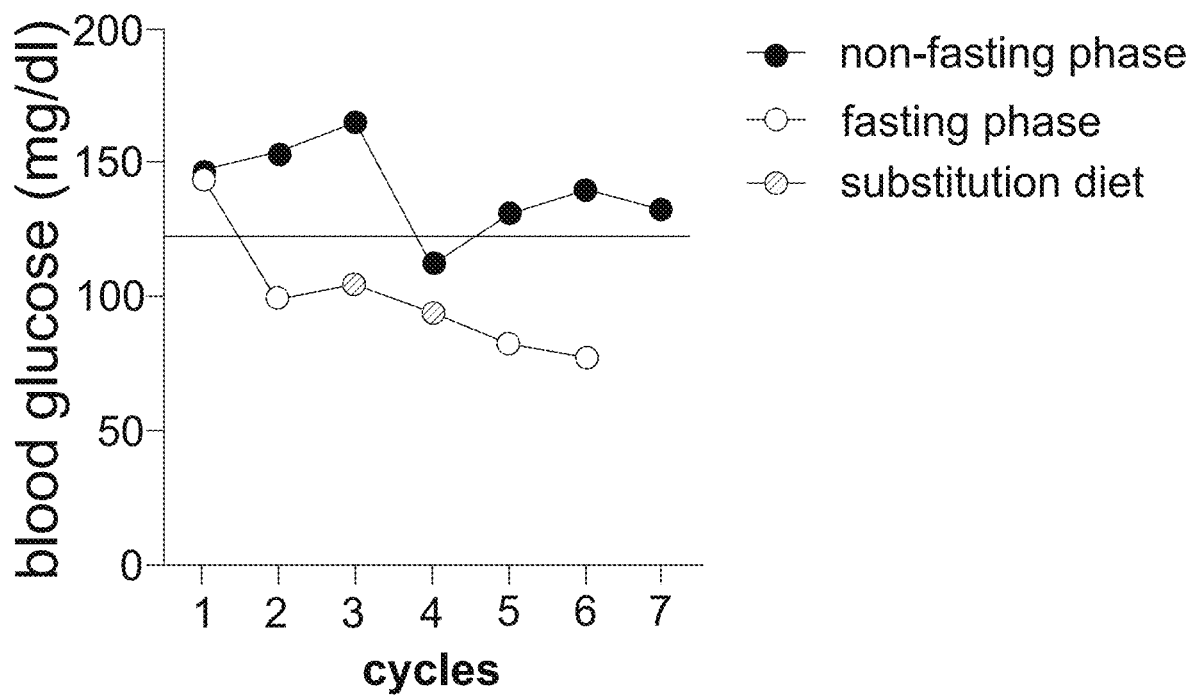
FIG. 6. Effect of Fasting and a Fasting Mimicking Diet (as described in FMD1 and FMD2 sections) in a pre-diabetic human subject. Fasting plasma glucose (FPG) levels in a pre-diabetic subject who underwent multiple cycles of a FMD. Reduction in blood glucose was found after cycles of fasting/diet cycles, at both the non-fasting phase and fasting/diet phase. Horizontal line indicates the level for identifying pre-diabetes (FPG 110-125 mg/dl).

FIG. 6 provides the effect of Fasting and a Fasting Mimicking Diet (as described in FMD1 and FMD2 sections) in a pre-diabetic human subject. With respect to fasting plasma glucose (FPG) levels in a pre-diabetic subject who underwent multiple cycles of a FMD, reduction in blood glucose was found after cycles of fasting/diet cycles, at both the non-fasting phase and fasting/diet phase. The horizontal line indicates the level for identifying pre-diabetes (FPG 110-125 mg/dl).

Human FMD Trials

Figure 7:
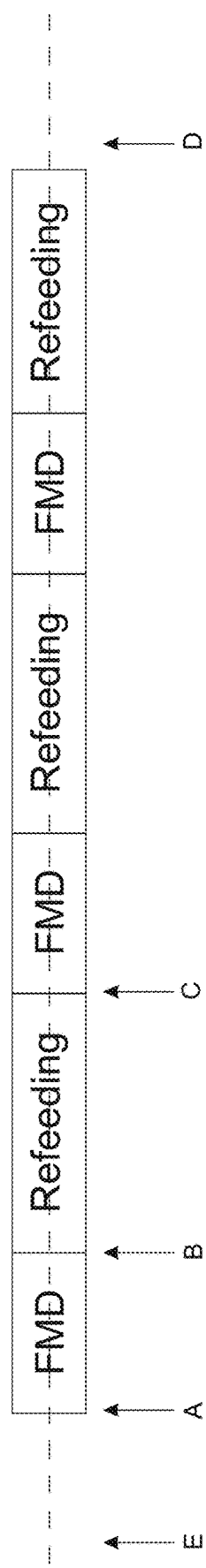
FIG. 7. An experimental scheme of a human adapted version of the Fasting Mimicking Diet (FMD).

FIG. 7 illustrates an experimental scheme of a human adapted version of the Fasting Mimicking Diet (FMD). FMD was supplied to participants once per month for 3 consecutive cycles. Each cycle consists of 5 days of FMD and 25 days of refeeding. Biomedical measurements presented below were performed at baseline (E) and prior to the start of the diet (A), immediately after the first FMD cycle (B) and during the refeeding period after the 1st cycle (C) and that after 3 cycles of FMD+Refeeding (D).

Figure 8:
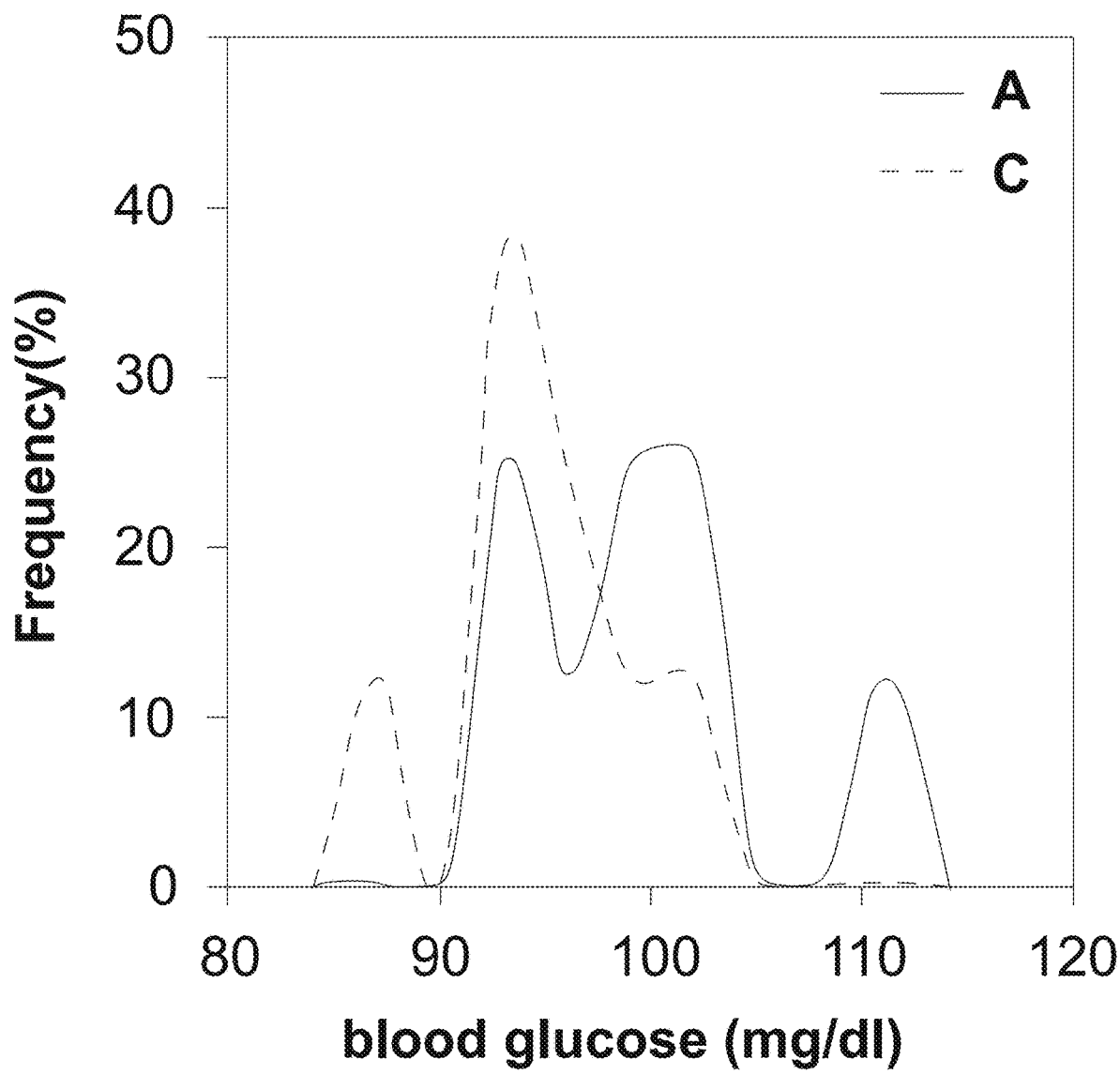
FIG. 8 provides the distribution of fasting blood glucose of human subjects before (A) and after (C) receiving FMD.

FIG. 8 provides the distribution of fasting blood glucose of human subjects. FMD reduces blood glucose levels in human subjects originally with high basal blood glucose (baseline >90 mg/dl). Fasting blood glucose was measured at indicated time points: A, before receiving FMD; C, 7 days of refeeding after 1st FMD. See also FIG. 7 for the experimental scheme. N=16.

Table 5 provides the levels of fasting blood glucose of human subjects before and after receving FMD. FMD reduces blood glucose levels in human subjects with high basal blood glucose (>90 mg/dl) (p<0.05, t-test). Fasting blood glucose was measured at indicated time points: pre-FMD, tme point A, before receiving FMD; post-FMD, time point C, 7 days of refeeding after 1st FMD. See also FIG. 7 for the experimental scheme.

TABLE 5

Levels of fasting blood glucose of human subjects before and after receving FMD

|  | pre-FMD (n = 8) | post-FMD (n = 8) |
| --- | --- | --- |
| Minimum | 93.00 | 87.00 |
| 25% Percentile | 94.63 | 93.00 |
| Median | 98.25 | 95.00 |
| 75% Percentile | 102.5 | 97.50 |
| Maximum | 109.5 | 101.0 |

Tables 6A and 6B gives the homeostasis model assessment of insulin resistance (HOMA-IR) and beta cell function (% B) of human subjects on FMD. HOMA-IR and % B at indicated time points are used here to evaluate the contribution of insulin sensitivity or beta cell function to the effects of FMD on steady-state glucose homeostasis. Indexes were calculated using fasting blood glucose and plasma insulin levels at indicated time points: E, baseline; A, before FMD; B, at the end of 1st FMD; C, refeeding period after 1st FMD; D refeeding period after 3 cycles of FMD. Trends of induction or reduction were indicated by the arrows. See also FIG. 7 for the experimental scheme.

TABLE 6A

Homeostasis model assessment of insulin resistance (HOMA-IR)

| HOMA-IR | E (n = 3) | A (n = 11) | B (n = 10) | C (n = 6) | D (n = 2) |
|---|---|---|---|---|---|
| Minimum | 0.38 | 0.4363 | 0.3472 | 0.4363 | 0.6741 |
| 25% Percentile | 0.38 | 0.5254 | 0.4223 | 0.6702 | 0.6741 |
| Median | 0.9086 | 0.958 | 0.5215↓↓ | 1.472 | 0.8926↓ |
| 75% Percentile | 1.59 | 2.346 | 0.8414 | 2.054 | 1.111 |
| Maximum | 1.59 | 3.111 | 2.336 | 2.77 | 1.111 |
| Mean ± SEM | 0.96 ± 0.35 | 1.35 ± 0.30 | 0.73 ± 0.19 | 1.45 ± 0.34 | 0.89 ± 0.0.22 |

TABLE 6B

Homeostasis model assessment of beta cell function (HOMA % B).

| HOMA % B | E (n = 3) | A (n = 11) | B (n = 10) | C (n = 6) | D (n = 2) |
|---|---|---|---|---|---|
| Minimum | 38 | 13.96 | 20.73 | 22.8 | 38.57 |
| 25% Percentile | 38 | 19.54 | 26.47 | 27.02 | 38.57 |
| Median | 49.66 | 42.35 | 56.81↑↑ | 57.27 ↑↑ | 52.62↑ |
| 75% Percentile | 86.9 | 90 | 94.47 | 103.8 | 66.67 |
| Maximum | 86.9 | 112.5 | 225 | 110.8 | 66.67 |
| Mean ± SEM | 58.18 ± 14.75 | 50.97 ± 10.84 | 76.34 ± 21.44 | 63.01 ± 14.9 | 52.62 ± 14.05 |

Figure 9:
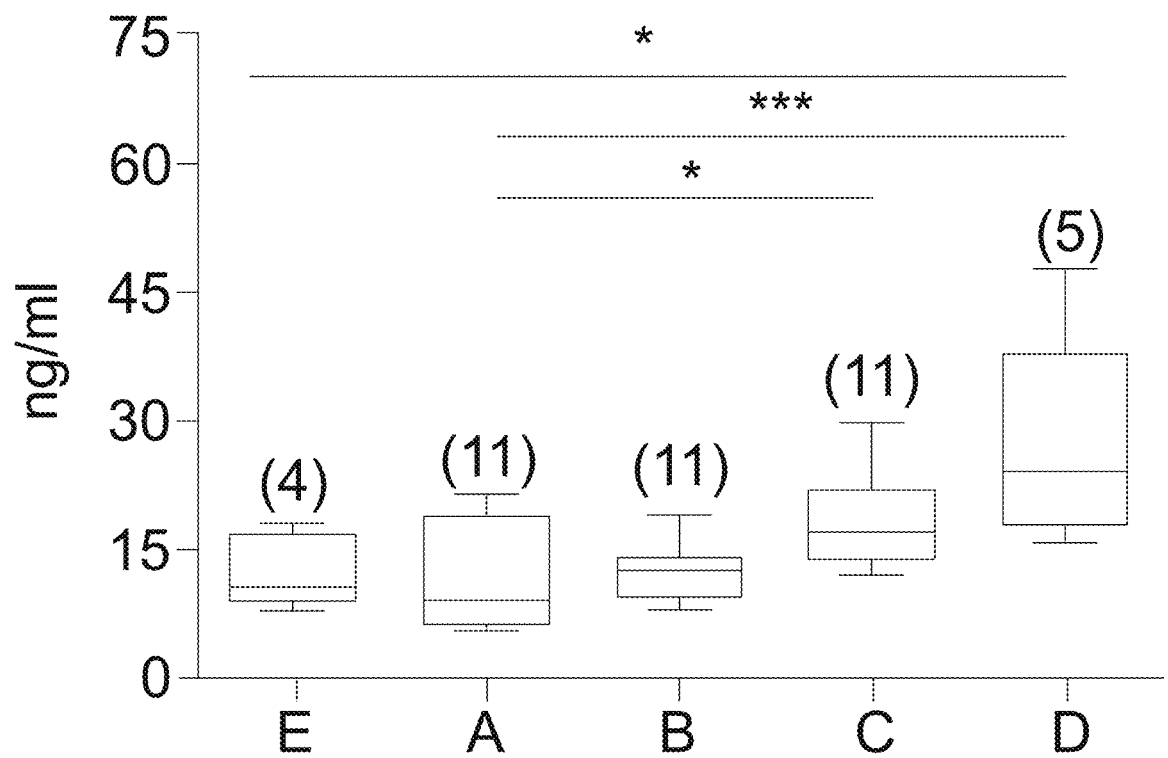
FIG. 9. Circulating levels of betatrophin, shown to cause pancreatic beta cell regeneration, were increased at post-FMD refeeding.

FIG. 9 provides plots of circulating betatrophin levels for human subjects. Sample size is indicated in parentheses. It is observed that betatrophin levels were increased at post-FMD refeeding compared to the baseline and before administration of the FMD.

Table 7 shows that levels of adiponectin in the serum of human subjects on FMD were measured at baseline and after 3 cycles of the FMD, indicating a 40% increase in circulating adiponectin after 3 cycles of the diet (post-FMD, 7 days refeeding after cycle 3). Higher adiponectin levels are associated with insulin sensitization and a lower risk of type 2 diabetes.

TABLE 7

Levels of Adiponectin of human subjects before and after receiving 3 cycles of the FMD.

|  | pre-FMD | post-FMD |
|---|---|---|
| N | 1 | 1 |
| Mean | 100 | 140.1 ± 29.04 |

Figure 10:
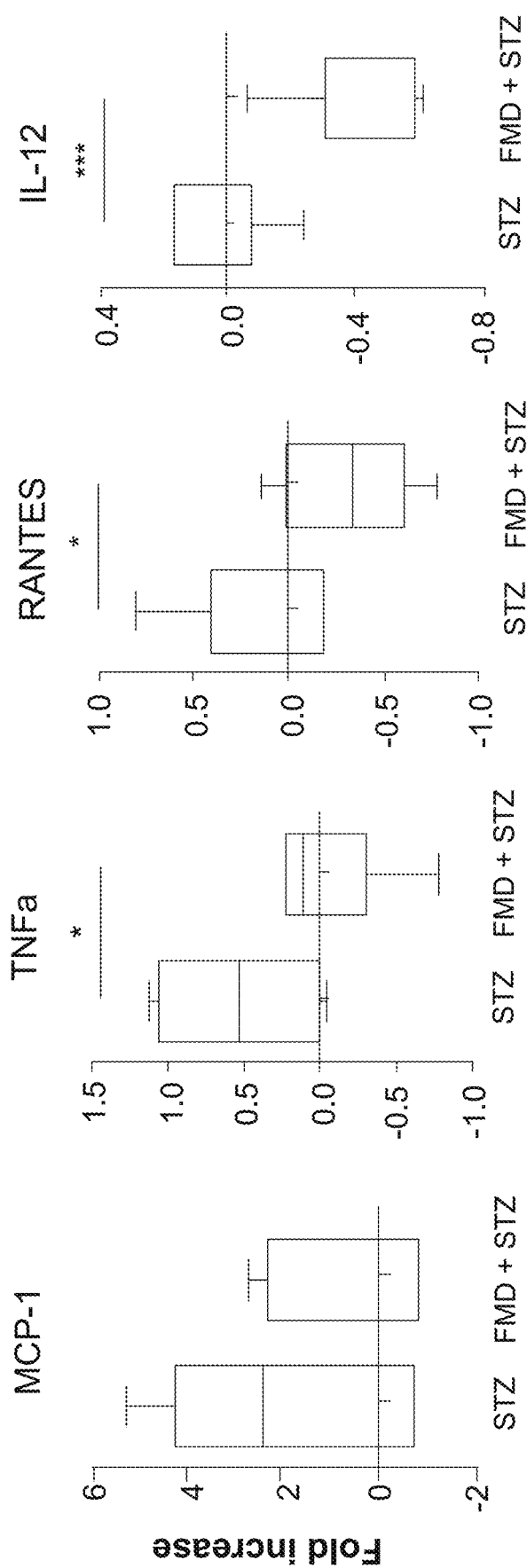
FIG. 10. FMD cycles showing a reduction in cytokines associated with autoimmune type 1 diabetes in mice.

FIG. 10 provides charts of FMD cycles showing a reduction in cytokines associated with autoimmune type 1 diabetes in mice. MCP-1, TNFa, RANTES and IL-12 are known to be associated with the autoimmune pathogenesis of type 1 diabetes. In the Streptozotocin (STZ)-induced T1D mouse model, levels of the indicated inflammatory cytokines in serum were reduced after 8 cycles of FMD treatment.

Table 8 provides the effects of FMD on immune cells in mice. Cytotoxic CD8+ T-cells have a major role in pathogenesis of type 1 diabetes. Numbers of cells ($10^6$/ml) in the peripheral blood of STZ-induced T1D model were measured at the $8^{th}$ cycle of the indicated timepoints, indicating a reduction of circulating T-cell populations in mice on FMD cycles. AL, ad libitum fed mice; FMD, at the end of FMD; post-FMD, 7 days after post-FMD refeeding.

TABLE 8

Effects of FMD on immune cells in mice

|  | AL | FMD | post-FMD |
|---|---|---|---|
| WBC | 10.39 ± 1.1 | 6.81 ± 1.6 ↓ | 9.23 ± 1.3 |
| Total T cell | 2.62 ± 0.34 | 1.34 ± 0.17 ↓↓ | 2.18 ± 0.30↓ |
| CD8+ T cell | 1.03 ± 0.2 | 0.58 ± 0.1 ↓ | 0.34 ± 0.14 ↓↓ |

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A diet package for administering a fasting mimicking diet, the diet package comprising:
   rations for the fasting mimicking diet to be administered for a first time period to a subject, the first time period including a first day, a second day, a third day, a fourth day, and a fifth day, the rations for the fasting mimicking diet providing less than about 50% of the normal caloric intake of the subject wherein the rations for the fasting mimicking diet includes protein in an amount that is less than 15 percent of total calories provided by the rations for the fasting mimicking diet and sugars in an amount that is less than 15 percent of total calories provided by the rations for the fasting mimicking diet, the rations providing less than 12 g of saturated fats on the first day and less than 6 grams of saturated fats on the second to fifth days.

2. The diet package of claim 1, wherein the diet package includes rations for 2 to 6 days.

3. The diet package of claim 1, wherein the diet package includes rations for 4 or 5 days.

4. The diet package of claim 1, wherein the rations for the fasting mimicking diet provides from 4.5 to 7 kilocalories per pound of subject for the first day and 3 to 5 kilocalories per pound of subject per day for a second to fifth days, the fasting mimicking diet being a low protein diet that provides less than 28 g of proteins on the first day and less than 18 g of proteins on the second to fifth wherein the rations provide less than 30 g of sugar on the first day, less than 20 g of sugar on the second to fifth days, 20 to 30 grams of monounsaturated fats on the first day and 10 to 15 grams of monounsaturated fats on the second to fifth days.

5. The diet package of claim 1, wherein the rations provide between 6 and 10 grams of polyunsaturated fats on the first day and 3 to 5 grams of polyunsaturated fats on the second to fifth days.

6. The diet package of claim 1, wherein the rations provide 2 to 5% calories from glycerol.

7. The diet package of claim 1, wherein the rations provide at least 60% calories from fatty acids, 2-5% calories from glycerol, up to 5% of calories from plant-based proteins, and a maximum of 35% of calories from carbohydrates.

8. The diet package of claim 1, wherein the rations provide 12 to 25 grams of glycerol per day on the second to fifth days.

9. The diet package of claim 1, wherein the rations provide over 5,000 IU of vitamin A per day for days 1-5 and 60-240 mg of vitamin C per day for days 1-5.

10. The diet package of claim 9, wherein the rations provide 400-800 mg of calcium per day for days 1-5; 7.2-14.4 mg of iron per day for days 1-5; 200-400 mg of magnesium per day for days 1-5; 1-2 mg of copper per day for days 1-5; 1-2 mg of manganese per day for days 1-5; and 3.5-7 mcg of selenium per day for days 1-5.

11. The diet package of claim 9, wherein for a five-day period, the rations provide 2-4 mg of Vitamin B1 per day for days 1-5; 2-4 mg of Vitamin B2 per day for days 1-5; 20-30 mg of Vitamin B3 per day for days 1-5; 1-1.5 mg of Vitamin B5 per day for days 1-5; 2-4 mg of Vitamin B6 per day for days 1-5; 240-480 mcg of Vitamin B9 per day for days 1-5; 600-1000 IU of Vitamin D per day for days 1-5; 14-30 mg of Vitamin E per day for days 1-5; over 80 mcg of Vitamin K per day for days 1-5; and 16-25 mcg Vitamin B12 are provided during the 5-day period.

12. The diet package of claim 9, wherein the rations provide 600 mg of docosahexaenoic acid during the 5 day period.

13. A diet package for administering a fasting mimicking diet, the diet package comprising:
rations for the fasting mimicking diet to be administered for a first time period to a subject, the first time period including a first day, a second day, a third day, a fourth day, and a fifth day, the rations for the fasting mimicking diet providing less than about 50% of the normal caloric intake of the subject wherein the rations for the fasting mimicking diet includes protein in an amount that is less than 15 percent of total calories provided by the rations for the fasting mimicking diet and sugars in an amount that is less than 15 percent of total calories provided by the rations for the fasting mimicking diet, the rations providing less than 12 g of saturated fats on the first day and less than 6 grams of saturated fats on the second to fifth days and wherein the diet package includes rations for 4 or 5 days.

14. The diet package of claim 13, wherein the rations provide 2 to 5% calories from glycerol.

15. The diet package of claim 13, wherein the rations provide at least 60% calories from fatty acids, 2-5% calories from glycerol, up to 5% of calories from plant-based proteins, and a maximum of 35% of calories from carbohydrates.

16. The diet package of claim 13, wherein the rations provide over 5,000 IU of vitamin A per day for days 1-5 and 60-240 mg of vitamin C per day for days 1-5.

17. The diet package of claim 13, wherein the rations provide 400-800 mg of calcium per day for days 1-5; 7.2-14.4 mg of iron per day for days 1-5; 200-400 mg of magnesium per day for days 1-5; 1-2 mg of copper per day for days 1-5; 1-2 mg of manganese per day for days 1-5; and 3.5-7 mcg of selenium per day for days 1-5.

18. The diet package of claim 13, wherein the rations provide 600 mg of docosahexaenoic acid during the 5-day period.

19. A method of alleviating a symptom of diabetes, the method administering the diet package of claim 1 to the subject when the subject is identified as exhibiting symptoms caused by pancreatic beta cell destruction.

20. A method of alleviating insulin resistance and/or hyperglycemia, the method administering the diet package of claim 1 to the subject when the subject is identified as having or being predisposed to insulin resistance and/or fasting hyperglycemia diabetes.

* * * * *